United States Patent
Ichim et al.

(10) Patent No.: US 12,011,462 B2
(45) Date of Patent: Jun. 18, 2024

(54) STIMULATION OF MESENCHYMAL STEM CELL THERAPEUTIC ACTIVITIES BY T REGULATORY CELLS

(71) Applicant: Therapeutic Solutions International, Inc., Oceanside, CA (US)

(72) Inventors: Thomas E. Ichim, Oceanside, CA (US); Famela Ramos, Oceanside, CA (US); James Veltmeyer, Oceanside, CA (US); Timothy G. Dixon, Oceanside, CA (US); Feng Lin, Oceanside, CA (US); Kalina O'Connor, Oceanside, CA (US)

(73) Assignee: Therapeutic Solutions International, Inc, Oceanside, CA (US)

( * ) Notice: Subject to any disclaimer, the term of this patent is extended or adjusted under 35 U.S.C. 154(b) by 0 days.

(21) Appl. No.: 17/934,460

(22) Filed: Sep. 22, 2022

(65) Prior Publication Data

US 2023/0090980 A1  Mar. 23, 2023

Related U.S. Application Data

(60) Provisional application No. 63/247,016, filed on Sep. 22, 2021.

(51) Int. Cl.
*A61K 35/17* (2015.01)
*A61K 35/28* (2015.01)
*A61P 11/00* (2006.01)

(52) U.S. Cl.
CPC .............. *A61K 35/17* (2013.01); *A61K 35/28* (2013.01); *A61P 11/00* (2018.01)

(58) Field of Classification Search
None
See application file for complete search history.

(56) References Cited

PUBLICATIONS

Lin, Feng; et al; "Mesenchymal stem cells as living anti-inflammatory therapy for COVID-19 related acute respiratory distress syndrome" World Journal of Stem Cells, 26, 1067-1079, 2020 (Year: 2020).*

Gladstone, Douglas; et al; "Regulatory T Cells for Treating Patients With COVID-19 and Acute Respiratory Distress Syndrome: Two Case Reports" Annals of Internal Medicine, L20-0681, 2020 (Year: 2020).*

Caplan, Henry W; et al; "Combination therapy with Treg and mesenchymal stromal cells enhances potency and attenuation of inflammation after traumatic brain injury compared to monotherapy" Stem Cells, 39, 358-370, 2021 (Year: 2021).*

(Continued)

*Primary Examiner* — David W Berke-Schlessel
(74) *Attorney, Agent, or Firm* — Baumgartner Patent Law, LLC; Marc Baumgartner

(57) ABSTRACT

Disclosed are novel means of enhancing mesenchymal stem cell regenerative activities including, intra alia, production from pulmonary leakage and suppression of scar tissue formation by co-administration with T regulatory cells. In some embodiments the invention provides an interaction between T regulatory cells and mesenchymal stem cells in which T regulatory cells stimulate upregulation of mesenchymal stem cell activity in a GITR dependent manner.

12 Claims, 2 Drawing Sheets

(56) References Cited

PUBLICATIONS

Wang, Wendi; et al; "Therapeutic mechanisms of mesenchymal stem cells in acute respiratory distress syndrome reveal potentials for Covid-19 treatment" Journal, of Translational Medicine, 19, 2021 (Year: 2021).*

Li, Xudong; Zheng, Ye; "Regulatory T cell identity: formation and maintenance" Trends in Immunology, 36, 344-353, 2016 (Year: 2016).*

* cited by examiner

STIMULATION OF MESENCHYMAL STEM CELL THERAPEUTIC ACTIVITIES BY T REGULATORY CELLS

CROSS-REFERENCE TO RELATED APPLICATIONS

This application claims priority to U.S. Provisional Application Ser. No. 63/247,016, filed Sep. 22, 2021, which is hereby incorporated by reference in its entirety.

FIELD OF THE INVENTION

The invention pertains to the field of stem cell therapeutics, more particularly the invention pertains to the field of pulmonary injury treatment using stem cells, more particularly the invention provides a novel means of inducing upregulation of stem cell activity by administration of T regulatory cells.

BACKGROUND

At the time of patent filing, the SARS-CoV-2 (previously known as 2019-nCoV), is spreading rapidly around the world, causing pandemic in a sharp rise of a pneumonia-like disease termed Coronavirus Disease 2019 (COVID-19) [1, 2]. COVID-19 presents a high mortality rate, estimated at 3.4% by the World Health Organization [3]. The rapid spread of the virus (estimated reproductive number $R_0$ 2.2-3.6 [4, 5] is causing a significant surge of patients requiring intensive care. More than 1 out of 4 hospitalized COVID-19 patients have required admission to an Intensive Care Unit (ICU) for respiratory support, and a large proportion of these ICU-COVID-19 patients, between 17% and 46%, have died [6-10]. A common observation among patients with severe COVID-19 infection is an inflammatory response localized to the lower respiratory tract [11-13]. This inflammation, associated with dyspnea and hypoxemia, in some cases evolves into excessive immune response with cytokine storm, determining progression to Acute Lung Injury (ALI), Acute Respiratory Distress Syndrome (ARDS), organ failure, and death [2, 10]. Draconian measures have been put in place in an attempt to curtail the impact of the COVID-19 epidemic on population health and healthcare systems. However, WHO has now classified COVID-19 a pandemic [3]. At the present time, there is neither a vaccine nor specific antiviral treatments for seriously ill patients infected with COVID-19. Crucially, no options are available for those patients with rapidly progressing ARDS evolving to organ failure. Although supportive care is provided whenever possible, including mechanical ventilation and support of vital organ functions, it is insufficient in most severe cases. Therefore, there is an urgent need for novel therapies that can dampen the excessive inflammatory response in the lungs, associated with the immunopathological cytokine storm, and accelerate the regeneration of functional lung tissue in COVID-19 patients.

SUMMARY

Preferred embodiments include methods of inhibiting lung inflammation by administration of a T regulatory cell population together with a mesenchymal stem cell population.

Preferred methods include embodiments wherein said T regulatory cells express FoxP3.

Preferred methods include embodiments wherein said T regulatory cells express TGF-beta.

Preferred methods include embodiments wherein said T regulatory cells express Helios.

Preferred methods include embodiments wherein said T regulatory cells express CD25.

Preferred methods include embodiments wherein said T regulatory cells express interleukin-10.

Preferred methods include embodiments wherein said T regulatory cells express CTLA-4.

Preferred methods include embodiments wherein said mesenchymal stem cell population expresses CD105.

Preferred methods include embodiments wherein said mesenchymal stem cell population expresses CD90.

Preferred methods include embodiments wherein said mesenchymal stem cell population expresses c-kit.

Preferred methods include embodiments wherein said mesenchymal stem cell population expresses FGF-2.

Preferred methods include embodiments wherein said mesenchymal stem cell population expresses OCT-2.

Preferred methods include embodiments wherein said mesenchymal stem cell population expresses KLF.

Preferred methods include embodiments wherein said mesenchymal stem cell population expresses SOX-2.

Preferred methods include embodiments wherein said mesenchymal stem cell population expresses NANOG.

Preferred methods include embodiments wherein said mesenchymal stem cell population is pretreated with an activator of indolamine 2-3 deoxygenase.

Preferred methods include embodiments wherein said activator of indolamine 2-3 deoxygenase is interferon alpha.

Preferred methods include embodiments wherein said activator of indolamine 2-3 deoxygenase is interferon gamma.

Preferred methods include embodiments wherein said activator of indolamine 2-3 deoxygenase is interferon beta.

Preferred methods include embodiments wherein said activator of indolamine 2-3 deoxygenase is interleukin-33.

Preferred methods include embodiments wherein said lung inflammation is ARDS.

Preferred methods include embodiments wherein said lung inflammation is caused by COVID-19.

Preferred methods include embodiments wherein said lung inflammation is lung fibrosis.

DETAILED DESCRIPTION OF THE INVENTION

Figure 1:
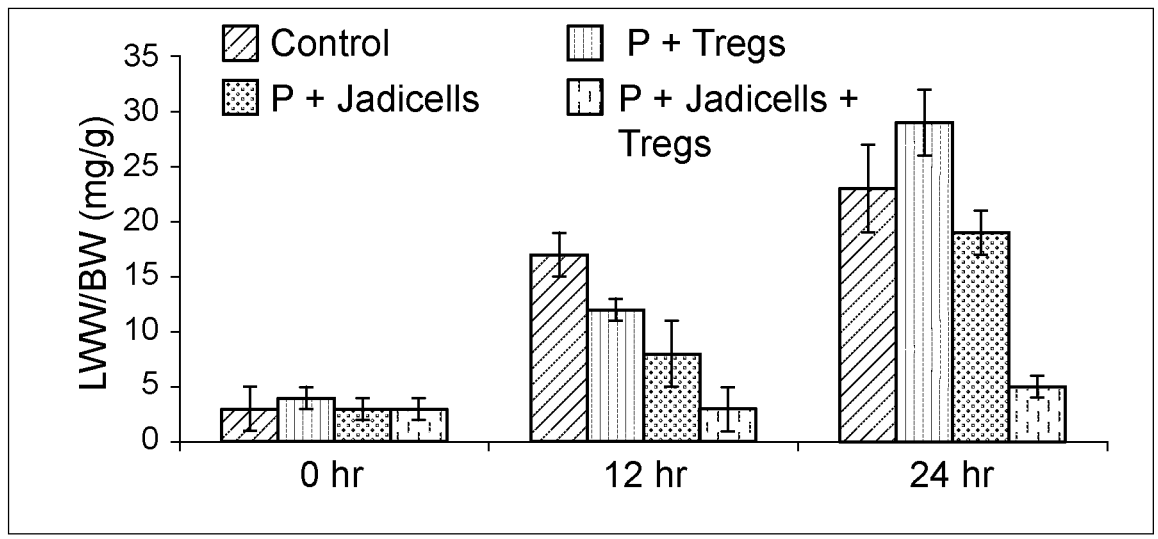
FIG. 1 is a bar graph showing Treg and JADI CELL™ Synergy in a LPS Model of BALB/c mice.

The invention provides novel means of enhancing therapeutic activities of mesenchymal stem cells by administration of T cells. In specific embodiments the T cells administered are T regulatory cells.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

As used herein, unless explicitly stated otherwise or clearly implied otherwise the terms 'therapeutically effective dose,' 'therapeutically effective amounts,' and the like, refers to a portion of a compound that has a net positive effect on the health and wellbeing of a human or other animal. Therapeutic effects may include an improvement in longevity, quality of life and the like these effects also may also include a reduced susceptibility to developing disease or deteriorating health or wellbeing. The effects may be immediate realized after a single dose and/or treatment or they may be cumulative realized after a series of doses and/or treatments.

The invention teaches the use of T regulatory cells to prevent, inhibit or reverse ARDS. In one embodiment, the invention provides for administration of exogenous T regulatory cells in a patient at risk of ARDS or suffering from ARDS. In another embodiment, the invention provides the use of agents which augment activity and/or number of endogenous T regulatory cells.

In some embodiments of the invention, stimulation of T regulatory cells in vivo is accomplished by administration of Aldesleukin (Proleukin, Novartis), which is a commercially available IL-2 licensed for the treatment of metastatic renal cell carcinoma in the UK. It is produced by recombinant DNA technology using an *Escherichia coli* strain, which contains a genetically engineered modification of the human IL-2 gene, and is administered either intravenously or subcutaneously (SC). Following short intervenous infusion, its pharmacokinetic profile is typified by high plasma concentrations, rapid distribution into the extravascular space and a rapid renal clearance. The recommended doses for continuous infusion and subcutaneous injection (as detailed in the Summary of Product Characteristics) are repeated cycles of $18\times10^6$ IU per m$^2$ per 24 hours for 5 days and repeated doses of $18\times10^6$ IU, respectively. Peak plasma levels are reached in 2-6 hours after SC administration, with bioavailability of aldesleukin ranging between 31% and 47%. The process of absorption and elimination of subcutaneous aldesleukin is described by a one-compartment model, with a 45 min absorption half-life and an elimination half-life of 3-5 hours [14]. Natural IL-2 was first identified in 1976 as a growth factor for T lymphocytes. It is produced by human cluster designation (CD) 4+ and some CD8+ T-cells and is synthesized mainly by activated T-cells, in particular CD4.sup.+ helper T cells. It stimulates the proliferation and differentiation of T cells, induces the generation of cytotoxic T lymphocytes (CTLs) and the differentiation of peripheral blood lymphocytes to cytotoxic cells and lymphokine-activated killer (LAK) cells, promotes cytokine and cytolytic molecule expression by T cells, facilit:ites the proliferation and differentiation of B-cells and the synthesis of immunoglobulin by B-cells, and stimulates the generation, proliferation and activation of natural killer (NK). IL-2 is known to play a central role in the generation of immune responses. In cancer clinical trials, high-dose recombinant IL-2 (e.g., IV bolus dose of 600,000 international units (IU)/kg every 8 hours for up to 14 doses) demonstrated antitumor activity in metastatic renal cell carcinoma (RCC) and metastatic melanoma. Accordingly, such high-dose IL-2 was approved for the treatment of metastatic RCC in Europe in 1989 and in the US in 1992. In 1998, approval was obtained to treat patients with metastatic melanoma. Recombinant human IL-2 (Aldesleukin) (Proleukin®-Novartis Inc. & Prometheus Labs Inc.) is currently approved by the United States Food and Drug Administration (US FDA). However, IL-2 has a dual function in the immune response in that it not only mediates expansion and activity of effector cells, but also is crucially involved in maintaining peripheral immune tolerance. A major mechanism underlying peripheral self-tolerance is IL-2 induced activation-induced cell death (AICD) in T cells. AICD is a process by which fully activated T cells undergo programmed cell death through engagement of cell surface-expressed death receptors such as CD95 (also known as Fas) or the TNF receptor. When antigen-activated T cells expressing a high-affinity IL-2 receptor (after previous exposure to IL-2) during proliferation are re-stimulated with antigen via the T cell receptor (TCR)/CD 3 complex, the expression of Fas ligand (FasL) and/or tumor necrosis factor (TNF) is induced, making the cells susceptible for Fas-mediated apoptosis. This process is IL-2 dependent and mediated via STATS. By the process of AICD in T lymphocytes tolerance can not only be established to self-antigens, but also to persistent antigens that are clearly not part of the host's makeup, such as tumor antigens.

In some embodiments of the invention, administration of angiogenic genes is performed in the lung to enhance efficacy of Treg cell therapy. Genes with angiogenic ability include: activin A, adrenomedullin, aFGF, ALK1, ALK5, ANF, angiogenin, angiopoietin-1, angiopoietin-2, angiopoietin-3, angiopoietin-4, bFGF, B61, bFGF inducing activity, cadherins, CAM-RF, cGMP analogs, ChDI, CLAF, claudins, collagen, connexins, Cox-2, ECDGF (endothelial cell-derived growth factor), ECG, ECI, EDM, EGF, EMAP, endoglin, endothelins, endostatin, endothelial cell growth inhibitor, endothelial cell-viability maintaining factor, endothelial differentiation shingoingolipid G-protein coupled receptor-1 (EDG1), ephrins, Epo, HGF, TGF-beta, PD-ECGF, PDGF, IGF, IL8, growth hormone, fibrin fragment E, FGF-5, fibronectin, fibronectin receptor, Factor X, HB-EGF, HBNF, HGF, HUAF, heart derived inhibitor of vascular cell proliferation, Ill, IGF-2 IFN-gamma, α1β1 integrin, α2β1 integrin, K-FGF, LIF, leiomyoma-derived growth factor, MCP-1, macrophage-derived growth factor, monocyte-derived growth factor, MD-ECI, MECIF, MMP2, MMP3, MMP9, urokiase plasminogen activator, neuropilin, neurothelin, nitric oxide donors, nitric oxide synthases (NOSs), notch, occludins, zona occludins, oncostatin M, PDGF, PDGF-B, PDGF receptors, PDGFR-β, PD-ECGF, PAI-2, PD-ECGF, PF4, P1GF, PKR1, PKR2, PPAR-gamma, PPAR-gamma ligands, phosphodiesterase, prolactin, prostacyclin, protein S, smooth muscle cell-derived growth factor, smooth muscle cell-derived migration factor, sphingosine-1-phosphate-1 (SIP1), Syk, SLP76, tachykinins, TGF-beta, Tie 1, Tie2, TGF-β, TGF-β receptors, TIMPs, TNF-α, transferrin, thrombospondin, urokinase, VEGF-A, VEGF-B, VEGF-C, VEGF-D, VEGF-E, VEGF, VEGF(164), VEGI, and EG-VEGF.

In one embodiment of the invention, patients suffering from ARDS are pretreated with $0.3\times10^6$ IU of aldesleukin daily. Concentrations for clinical uses of aldesleukin could be used from the literature as described for other indications including heart failure [14], Wiskott-Aldrich syndrome [15], Graft Versus Host Disease [16, 17], lupus [18], type 1 diabetes [19-21] and are incorporated by reference. In some embodiments of the invention, administration of low doses of IL-2 in the form of aldesleukin every day at concentrations of $0.3 \times 10^6$ to $3.0 \times 10^6$ IU IL-2 per square meter of body surface area for 8 weeks, or in other embodiments repetitive 5-day courses of $1.0 \times 10^6$ to $3.0 \times 10^6$ IU IL-2. Various types of IL-2 may be utilized. Examples of IL-2 variants, recombinant IL-2, methods of IL-2 production, methods of IL-2 purification, methods of formulation, and the like are well known in the art and can be found, for example, at least in U.S. Pat. Nos. 4,530,787, 4,569,790, 4,572,798, 4,604,377, 4,748,234, 4,853,332, 4,959,314, 5,464,939, 5,229,109, 7,514,073, and 7,569,215, each of which is herein incorporated by reference in their entirety for all purposes. In some embodiments, low dose interleukin-2 is provided together with activators of coinhibitory molecules, otherwise known as checkpoints. Such coinhibitory molecules include CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, A2aR, and combinations thereof. In some embodiments of the invention, mesenchymal stem cells are co-administered. Protocols for use of MSC have been previously published and incorporated by reference [22, 23]. For example, mesenchymal stem cells of adipose [24-27], bone marrow [28-47], placental [48], amniotic membrane [49, 50], umbilical cord [51-57], menstrual blood [58], and lung [59, 60], origin, as well as conditioned media [61-68]. Additionally, the generation of Treg by mesenchymal stem cells is also described in the art, for which we are providing the following references to assist in the practice of the invention [69-97].

In other embodiments, patients with ARDS are administered human IL-2 muteins that preferentially stimulate T regulatory (Treg) cells. As used herein "preferentially stimulates T regulatory cells" means the mutein promotes the proliferation, survival, activation and/or function of CD3+ FoxP3+ T cells over CD3+FoxP3– T cells. Methods of measuring the ability to preferentially stimulate Tregs can be measured by flow cytometry of peripheral blood leukocytes, in which there is an observed increase in the percentage of FOXP3+CD4+ T cells among total CD4+ T cells, an increase in percentage of FOXP3+CD8+ T cells among total CD8+ T cells, an increase in percentage of FOXP3+ T cells relative to NK cells, and/or a greater increase in the expression level of CD25 on the surface of FOXP3+ T cells relative to the increase of CD25 expression on other T cells. Preferential growth of Treg cells can also be detected as increased representation of demethylated FOXP3 promoter DNA (i.e. the Treg-specific demethylated region, or TSDR) relative to demethylated CD3 genes in DNA extracted from whole blood, as detected by sequencing of polymerase chain reaction (PCR) products from bisulfite-treated genomic DNA. IL-2 muteins that preferentially stimulate Treg cells increase the ratio of CD3+FoxP3+ T cells over CD3+ FoxP3– T cells in a subject or a peripheral blood sample at least 30%, at least 40%, at least 50%, at least 60%, at least 70%, at least 80%, at least 90%, at least 100%, at least 150%, at least 200%, at least 300%, at least 400%, at least 500%, at least 600%, at least 700%, at least 800%, at least 900%, or at least 1000%.

In some embodiments of the invention, patients suffering from ARDS are administered mesenchymal stem cells together with a tolerance inducing agent, said "agent" is meant to encompass essentially any type of molecule that can be used as a therapeutic to enhance T regulatory stimulating capable of mesenchymal stem cells administered in an allogeneic host. Proteins, such as antibodies, fusion proteins, and soluble ligands, any of which may either be identical to a wild-type protein or contain a mutation (i.e., a deletion, addition, or substitution of one or more amino acid residues), and the nucleic acid molecules that encode them (or that are "antisense" to them; e.g., an oligonucleotide that is antisense to the nucleic acids that encode a target polypeptide, or a component (e.g., a subunit) of their receptors), are all "agents." The agents of the invention can either be administered systemically, locally, or by way of cell-based therapies (i.e., an agent of the invention can be administered to a patient by administering a cell that expresses that agent to the patient). A tolerance restoring agent can be .alpha.1-antitrypsin (AAT; sometimes abbreviated AAT), which is also referred to as .alpha.1-proteinase inhibitor. AAT is a major serum serine-protease inhibitor that inhibits the enzymatic activity of numerous serine proteases including neutrophil elastase, cathespin G, proteinase 3, thrombin, trypsin and chymotrypsin. For example, one can administer an AAT polypeptide (e.g., a purified or recombinant AAT, such as human AAT) or a homolog, biologically active fragment, or other active mutant thereof. .alpha.1 proteinase inhibitors are commercially available for the treatment of AAT deficiencies, and include ARALAST™, PROLASTIN™ and ZEMAIRA™. The AAT polypeptide or the biologically active fragment or mutant thereof can be of human origin and can be purified from human tissue or plasma. Alternatively, it can be recombinantly produced. For ease of reading, we do not repeat the phrase "or a biologically active fragment or mutant thereof" after each reference to AAT. It is to be understood that, whenever a full-length, naturally occurring AAT can be used, a biologically active fragment or other biologically active mutant thereof (e.g., a mutant in which one or more amino acid residues have be substituted) can also be used. Similarly, we do not repeat on each occasion that a naturally occurring polypeptide (e.g., AAT) can be purified from a natural source or recombinantly produced. It is to be understood that both forms may be useful. Similarly, we do not repeatedly specify that the polypeptide can be of human or non-human origin. While there may be advantages to administering a human protein, the invention is not so limited.

The methods of the present invention (e.g., multiple-variable dose IL-2 alone or in combination with one or more other anti-immune disorder therapies) can be administered to a desired subject or once a subject is indicated as being a likely responder to such therapy. In another embodiment, the therapeutic methods of the present invention can be avoided if a subject is indicated as not being a likely responder to the therapy and an alternative treatment regimen, such as targeted and/or untargeted anti-immune therapies, can be administered.

In one embodiment, a multiple-variable IL-2 dose method of treating a subject suffering from ARDS a therapy comprising a) administering to the subject an induction regimen comprising continuously administering to the subject interleukin-2 (IL-2) at a dose that increases the subject's plasma IL-2 level and increases the subject's ratio of immune suppressive T cells to conventional T lymphocytes (Tcons) and b) subsequently administering to the subject at least one maintenance regimen comprising continuously administering to the subject an IL-2 maintenance dose that is higher than the induction regimen dose and that i) further increases the subject's plasma IL-2 level and ii) further increases the ratio of immune suppressive T cells to Tcons, thereby treating the subject, is provided. In one embodiment, the level of plasma IL-2 resulting from the induction regimen is depleted below that of the prior peak plasma IL-2 level before the induction regimen. The IL-2 maintenance regimen can, in certain embodiments, increase the subject's plasma IL-2 level beyond the peak plasma IL-2 level induced by the induction regimen. The term "multiple-variable IL-2 dose method" refers to a therapeutic intervention comprising more than one IL-2 administration, wherein the more than one IL-2 administration uses more than one IL-2 dose. Such a method is contrasted from a "fixed" dosed method wherein a fixed amount of IL-2 is administered in a scheduled manner, such as daily. The term "induction regimen" refers to the continuous administration of IL-2 at a dose that increases the subject's plasma IL-2 level and increases the subject's immune suppressive T cells:Tcons ratio. In some embodiments, the regimen occurs until a peak level of plasma IL-2 is achieved. The subject's plasma IL-2 level and/or immune suppressive T cell:Tcons ratio can be increased by at least 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200% or more relative to the baseline ratio prior to initiation of therapy.

In one embodiment of the invention certain doses and methods according to FDA-approved uses, Tcons are preferentially activated relative to immune suppressive T cells such that the immune suppressive T cells:Tcons ratio actually decreases. By contrast, the methods of the present invention increase the immune suppressive T cells:Tcons ratio by using "low-dose IL-2" in a range determined herein to preferentially promote immune suppressive T cells over Tcons and that are safe and efficacious in subjects suffering from ARDS.

The term "low-dose IL-2" refers to the dosage range wherein immune suppressive T cells are preferentially enhanced relative to Tcons. In one embodiment, low-dose IL-2 refers to IL-2 doses that are less than or equal to 50% of the "high-dose IL-2" doses (e.g., 18 million IU per m.sup.2 per day to 20 million IU per m.sup.2 per day, or more) used for anti-cancer immunotherapy. The upper limit of "low-dose IL-2" can further be limited by treatment adverse events, such as fever, chills, asthenia, and fatigue. IL-2 is generally dosed according to an amount measured in international units (IU) administered in comparison to body surface area (BSA) per given time unit. BSA can be calculated by direct measurement or by any number of well-known methods (e.g., the Dubois & Dubois formula), such as those described in the Examples. Generally, IL-2 is administered according in terms of IU per m.sup.2 of BSA per day. Exemplary low-dose IL-2 doses according to the methods of the present invention include, in terms of 10.sup.6 IU/m.sup.2/day, any one of 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0.times.10.sup.6 IU/m.sup.2/day, including any values in between and/or ranges in between. For example, an induction regimen dose can range between 0.3.times.10.sup.6 IU/m.sup.2/day and 3.0.times.10.sup.6 IU/m.sup.2/day with any value or range in between.

The term "continuous administration" refers to administration of IL-2 at regular intervals without any intermittent breaks in between. Thus, no interruptions in IL-2 occur. For example, the induction dose can be administered every day (e.g., once or more per day) during at least 1-14 consecutive days or any range in between (e.g., at least 4-7 consecutive days). As described herein, longer acting IL-2 agents and/or IL-2 agents administered by routes other than subcutaneous administration are contemplated. Intermittent intravenous administration of IL-2 described in the art results in short IL-2 half lives incompatible with increasing plasma IL-2 levels and increasing the immune suppressive T cells:Tcons ratio according to the present invention. However, once-daily subcutaneous IL-2 dosing, continuous IV infusion, long-acting subcutaneous IL-2 formulations, and the like are contemplated for achieving a persistent steady state IL-2 level.

As described above, IL-2 can be administered in a pharmaceutically acceptable formulation and by any suitable administration route, such as by subcutaneous, intravenous, intraperitoneal, oral, nasal, transdermal, or intramuscular administration. In one embodiment, the present invention provides pharmaceutically acceptable compositions which compose IL-2 at a therapeutically-effective amount, formulated together with one or more pharmaceutically acceptable carriers (additives) and/or diluents. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

In some embodiments of the invention the monoclonal antibody (mAb) against the CD3 molecule is utilized for immune modulation. This approach has previously been used to induced tolerance to autoimmunity in murine models of type 1 diabetes mellitus. Treatment with anti-CD3 mAb reversed diabetes in the NOD mouse and prevented recurrent immune responses toward transplanted syngeneic islets. This was achieved without the need for continuous immune suppression and persisted at a time when T cell numbers were not depleted and were quantitatively normal. Another approach is to induce specific immunological unresponsiveness by administering self-antigens.

For the practice of the invention, it is important to utilize the proper type of anti-CD3 antibody. The natural role of CD3 is to transduce signals in T cells from the T cell receptor into the nucleus of the T cells, usually to activity T cells. In some situations, antibodies to CD3 cause activation of T cells, not suppression. For example, Hirsch et al. investigated the ability of low dose anti-CD3 to enhance an anti-tumor response directed against the malignant murine UV-induced skin tumor. Low dose anti-CD3 administration resulted in enhanced in vitro anti-tumor activity and prevented tumor outgrowth in approximately two-thirds of animals treated at the time of tumor inoculation. Furthermore, these animals displayed lasting tumor-specific immunity. Augmentation of various parameters of immunity was noted. These results suggested that anti-CD3 mAb can be utilized for the enhancement of anti-tumor responses in vivo and may have general application in the treatment of immunodeficiency. They also point to the care that needs to be exercised when manipulating the CD3 pathway, given that the pathway can be both activatory or inhibitory [98]. Activatory signals by crosslinking CD3 are also seen in the tumor infiltrating lymphocyte (TIL) culture systems. It is known that early in the life of the TIL bulk culture, cytotoxicity is non-major histocompatibility complex restricted. Under these culture conditions antitumor cytotoxicity was observed to decline with increasing age of the bulk culture.

In addition, TIL became refractory to IL-2-induced expansion. In one study, scientists have used solid-phase anti-CD3 antibodies for TIL activation followed by culture in reduced concentrations of IL-2 to reactivate TIL previously grown in high concentrations of rIL-2. TIL refractory to IL-2 in terms of growth and antitumor cytotoxicity proved sensitive to anti-CD3 activation. The use of solid-phase anti-CD3 was also more effective than high concentrations of IL-2 in the expansion of TIL when used at the start of culture. Finally, TIL could be induced to secrete IL-2 following solid-phase activation with anti-CD3. These data suggest that human TIL are susceptible to activation by signals directed at the CD3 complex of the TIL cell surface [99].

An example of how different CD3 targeting antibodies can elicit different effects is seen in another study, which Davis et al. examined the IgM monoclonal antibody called 38.1, which was distinct from other anti-CD3 mAb, in that it was rapidly modulated from the cell surface in the absence of a secondary antibody. Although 38.1 induced an immediate increase in intracellular free calcium [Ca2+]i by highly purified T cells, it did not induce entry of the cells into the cell cycle in the absence of accessory cells (AC) or a protein kinase C-activating phorbol ester. Treated T cells were markedly inhibited in their capacity to respond to the T cell stimulating mitogen phytohemagluttanin. Inhibition of responsiveness could be overcome by culturing the cells with supplemental antigen presenting cells or the cytokine IL-2. These studies demonstrate that a state of T cell nonresponsiveness can be induced by modulating CD3 with an anti-CD3 mAb in the absence of co-stimulatory signals. A brief increase in [Ca2+]i resulting from mobilization of internal calcium stores appears to be sufficient to induce this state of T cell nonresponsiveness [100].

In some situations, anti-CD3 antibodies have been shown to program T cells towards antigen-specific tolerance. This is illustrated in one example in the work of Anasetti et al. who exposed PBMC to alloantigen for 3-8 d in the presence of anti-CD3 antibodies. They showed no response after restimulation with cells from the original donor but the PBMC remained capable of responding to third-party donors. Antigen-specific nonresponsiveness was induced by both nonmitogenic and mitogenic anti-CD3 antibodies but not by antibodies against CD2, CD4, CD5, CD8, CD18, or CD28. This suggested the unique ability of this protein to modulate programs in the T cells that are antigen specific. Nonresponsiveness induced by anti-CD3 antibody in mixed leukocyte culture was sustained for at least 34 d from initiation of the culture and 26 d after removal of the antibody. Anti-CD3 antibody also induced antigen-specific nonresponsiveness in cytotoxic T cell generation assays. Anti-CD3 antibody did not induce nonresponsiveness in previously primed cells [101].

The use of anti-CD3 antibodies for the practice of the invention requires that the antibodies not only do not result in activation of T cell proliferation and inflammatory cytokine secretion, but also that the T cells actually inhibit inflammation and promote regeneration.

In one embodiment of the invention, anti-CD3 antibody is given 14 days before administration of mesenchymal stem cells In one specific embodiment, said 14-day course of the anti-CD3 monoclonal antibody utilizes the antibody hOKT3γ1(Ala-Ala) administered intravenously (1.42 µg per kilogram of body weight on day 1; 5.67 µg per kilogram on day 2; 11.3 µg per kilogram on day 3; 22.6 µg per kilogram on day 4; and 45.4 µg per kilogram on days 5 through 14); these doses were based on those previously used for treatment of transplant rejection [102] which is incorporated by reference. Other types of anti-CD3 molecules and dosing regimens may be used in the context of ARDS therapeutics, said doses may be chosen from examples of utility of anti-CD3 from the literature, as described in the following papers and incorporated by reference: prevention of kidney [103-111], liver [112-114], pancreas [115-117], lung [118], and heart [119-123] transplant rejection; prevention of graft versus host disease [124], multiple sclerosis [125], type 1 diabetes [126].

The use of monoclonal antibodies for the practice of the invention must be tempered by the caution that in some cases cytokine storm may be initiated by antibody administration [127, 128]. In some cases this is concentration dependent [129]. Treatment for this can be accomplished by steroid administration or anti-IL6 antibody [130-134].

In some embodiments of the invention administration of PGE1 and/or various natural anti-inflammatory compounds are provided to decrease TNF-alpha production as a result of anti-CD3 administration, such as described in this paper and incorporated by reference [135]. In further embodiments of the invention, administration of anti-CD3 may be performed together with endothelial protectants and/or anti-coagulants in order to reduce clotting associated with CD3 modulating agents [136]. In some embodiments anti-CD3 antibodies may be used in combination with tolerogenic cytokines such as interleukin-10 in order to enhance number of angiogenesis supporting T cells. The safety of anti-CD3 and IL-10 administration has previously been demonstrated in a clinical trial [137].

In the current invention decreased TNF-alpha activity is correlated with enhancement of pulmonary regenerative activity. Furthermore, other inhibitors of TNF-alpha may be administered [138, 139].

In some embodiments of the invention, enhancement of pulmonary regenerative activity is provided by administration of oral modulators of CD3. Oral administration of OKT3 has been previously performed in a clinical trial and results are incorporated by reference [140, 141].

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate butler solutions; and (21) other non-toxic compatible substances employed in pharmaceutical formulations. Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

In one embodiment, the Treg cell surface protein is selected from the group consisting of CD25, GITR, TIGIT, CTLA-4, neuropilin, OX40, LAGS, and combinations thereof, said Tregs are isolated possessing said surfaces proteins from a tissue source, and optionally expanded ex vivo prior to administration to a patient suffering from ARDS.

The role of inflammatory cytokines in the progression of ARDS and its pathology may be seen in several situations. For example, tumor necrosis factor (TNF)-alpha, has been demonstrated to correlate with severity of ARDS in several studies. In one study, measure plasma TNF alpha levels (pl-TNF alpha) in 34 patients with ARDS and in 16 controls was examined. Plasma, TNF alpha was elevated in 76% of the patients with ARDS (71+/−104 pg/ml) and in 48% of the at-risk patients (47+/−73 pg/ml), providing some indication that TNF-alpha may correlated with ARDS [142]. In another study assessment of TNF-alpha was performed in fourteen hospitalized patients with a diagnosis of SARS-associated coronavirus infection. All patients had fever, dry cough and dyspnea. Twelve were intubated during hospitalization. The median duration from onset of fever to the nadir level or most severe condition was 9 days for hypoxia. The 8 patients who died possessed significantly higher peak levels of serum TNF-alpha compared to those who survived (14 vs 9.1 pg/mL; p=0.06) [143]. Another study demonstrated correlation between TNF-alpha and mortality. The study examined ICU patients on ventilator with (n=9) and without (n=12) evidence of ARDS. The median peak TNF concentration in control patients was 40 ng/L (range less than 40-100 ng/L) and in ARDS patients 231 ng/L (range 100-2550 ng/L; p less than 0.001). All of the control patients were discharged alive from the ICU, whereas 6 of 9 ARDS patients died in the ICU. In 6 ARDS patients, it was possible to measure more than 4 consecutive plasma TNF levels. Of these 6 patients, the 3 with persistent elevations in systemic TNF above 230 ng/L succumbed (p less than 0.05, one-tailed) [144].

It is believed the TNF-alpha production causes pathology in ARDS at several levels. In one experiment, TNF-alpha was administered intratracheally at 500 ng in healthy rats. It was observed that within 5 hours, lung lavage neutrophils, lung myeloperoxidase (MPO) activity, and lung leak was substantially higher in the treated as compared to saline-treated control rats [145]. In another study, it was shown that TNF-alpha maintains viability of neutrophils, thus allowing them to produce exaggerated inflammation responses. Scientists exposed neutrophils TNFalpha (100 ng/mL) in the presence or absence of antibodies to IL-8, and the extent of apoptosis was assessed. An enzyme-linked immunoassay was used to measure levels of the anti-apoptotic cytokine IL-8, induced by TNFalpha-stimulation. Because TNFalpha may mediate its effect through various cell-signaling pathways, the study next assessed the effect of kinase inhibition on the ability of TNFalpha to effect apoptosis and IL-8 production. Treatment with TNFalpha had a biphasic effect: at 4-8 h, apoptosis was increased but was markedly suppressed at 24 h (P<0.05). PMN cultured for 24 h with TNFalpha also showed markedly increased levels of IL-8. Neutralization of IL-8 inhibited the ability of TNFalpha to suppress apoptosis (P<0.05). These data illustrate a novel mechanism by which TNFalpha can indirectly elicit an anti-apoptotic effect via release of the anti-apoptotic chemokine IL-8 [146].

Perhaps one of the most tantalizing supporting evidences that TNF-alpha is a potential cause of ARDS are studies in which TNF-alpha was administered systemically as a cancer therapeutic and one of the adverse effects observed in some patients was a ARDS-type pathology [147].

Another cytokine which has been studied extensively in ARDS is interleukin-6. This cytokine is known to possess pro-inflammatory properties [148], as well as to suppress generation of T regulatory cells and promote Th17 cells [149-151]. It is accepted that in ARDS there is a reduction in T regulatory cells [152], whose role is tissue protection [153], and Th17 cells, which are commonly associated with inflammation [154]. In one study, 27 consecutive patients with severe medical ARDS. Plasma levels of tumor necrosis factor alpha (TNF-alpha) and interleukins (ILs) 1 beta, 2, 4, 6, and 8 were measured (enzyme-linked immunosorbent assay [ELISA] method) on days 1, 2, 3, 5, 7, 10, and 12 of ARDS and every third day thereafter while patients were receiving mechanical ventilation. Subgroups of patients were identified based on outcome, cause of ARDS, presence or absence of sepsis, shock, and MODS at the time ARDS developed. Subgroups were compared for levels of plasma inflammatory cytokines on day 1 of ARDS and over time. Of the 27 patients, 13 survived ICU admission and 14 died (a mortality rate of 52%). Overall mortality was higher in patients with sepsis (86 vs 38%, p<0.02). The mean initial plasma levels of TNF-alpha, IL-1 beta, IL-6, and IL-8 were significantly higher in nonsurvivors (p<0.0001) and in those patients with sepsis (p<0.0001). Plasma levels of IL-1 beta (p<0.01) and IL-6 (p=0.03) were more strongly associated with patient outcome than cause of ARDS (p=0.8), lung injury score (LIS), APACHE II score, sepsis (p=0.16), shock, or MODS score. Plasma levels of TNF-alpha, IL-1 beta, IL-6, and IL-8 remained significantly elevated over time (p<0.0001) in those who died. This study strongly supports the addition of IL-6 as another cytokine mediatory involved in the pathogenesis of ARDS [155].

A subsequent study examined 24 ARDS patients with MODS (ARDS+MODS group), 18 patients with ARDS but without MODS (ARDS group), and 55 patients with MODS but without ARDS as controls (control group). It was found that serum IL-6 levels in the ARDS+MODS group were significantly higher than those in the ARDS and MODS groups (P<0.01). The IL-6 levels increased with elevated ARDS illness severity (P<0.01); the sensitivity of IL-6 was high in all groups. Moreover, the IL-6 values were closely associated with patient survival [156]. Several other studies have shown correlation between IL-6 elevation and poor prognosis in ARDS [157-159].

In one embodiment of the invention, utilization of extracorporeal manipulations is used to generate an environment suitable of T regulatory survival after administration from exogenous sources, or to enhance survival of endogenous T regulatory cells. The extracorporeal removal of various physiological or pathological agents has been part of medical practice since the development of renal dialysis in the late 1940s by William Kolff [160]. Advanced means of extracorporeal removal of various substances has been demonstrated in the case of immune complex removal [161-164], antibodies [165-170], viruses [171-173], soluble receptors [174], and even cells [175, 176]. These methodologies may be used to optimize efficacy of the current invention.

In one embodiment of the invention, mesenchymal stem cell exosomes are administered in order to enhance therapeutic activity of T regulatory cells and/or low dose interleukin-2 therapy. Exosomes are purified from mesenchymal stem cells by obtaining a mesenchymal stem cell conditioned medium, concentrating the mesenchymal stem cell conditioned medium, subjecting the concentrated mesenchymal stem cell conditioned medium to size exclusion chromatography, selecting UV absorbent fractions at 220 nm, and concentrating fractions containing exosomes.

Exosomes, also referred to as "particles" may comprise vesicles or a flattened sphere limited by a lipid bilayer. The particles may comprise diameters of 40-100 nm. The particles may be formed by inward budding of the endosomal membrane. The particles may have a density of .about.1.13-1.19 g/ml and may float on sucrose gradients. The particles may be enriched in cholesterol and sphingomyelin, and lipid raft markers such as GM1, GM3, flotillin and the src protein kinase Lyn. The particles may comprise one or more proteins present in mesenchymal stem cells or mesenchymal stem cell conditioned medium (MSC-CM), such as a protein characteristic or specific to the MSC or MSC-CM. They may comprise RNA, for example miRNA. Said particles may possess one or more genes or gene products found in MSCs or medium which is conditioned by culture of MSCs. The particle may comprise molecules secreted by the MSC. Such a particle, and combinations of any of the molecules comprised therein, including in particular proteins or polypeptides, may be used to supplement the activity of, or in place of, the MSCs or medium conditioned by the MSCs for the purpose of for example treating or preventing a disease. Said particle may comprise a cytosolic protein found in cytoskeleton e.g. tubulin, actin and actin-binding proteins, intracellular membrane fusions and transport e.g. annexins and rab proteins, signal transduction proteins e.g. protein kinases, 14-3-3 and heterotrimeric G proteins, metabolic enzymes e.g. peroxidases, pyruvate and lipid kinases, and enolase-1 and the family of tetraspanins e.g. CD9, CD63, CD81 and CD82. In particular, the particle may comprise one or more tetraspanins. The particles may comprise mRNA and/or microRNA. The particle may be used for any of the therapeutic purposes that the MSC or MSC-CM may be put to use.

In one embodiment, MSC exosomes, or particles may be produced by culturing mesenchymal stem cells in a medium to condition it. The mesenchymal stem cells may comprise human umbilical tissue derived cells which possess markers selected from a group comprising of CD90, CD73 and CD105. The medium may comprise DMEM. The DMEM may be such that it does not comprise phenol red. The medium may be supplemented with insulin, transferrin, or selenoprotein (ITS), or any combination thereof. It may comprise FGF2. It may comprise PDGF AB. The concentration of FGF2 may be about 5 ng/ml FGF2. The concentration of PDGF AB may be about 5 ng/ml. The medium may comprise glutamine-penicillin-streptomycin or b-mercaptoethanol, or any combination thereof. The cells may be cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrane. The conditioned medium may be concentrated about 50 times or more. The conditioned medium may be subject to liquid chromatography such as HPLC. The conditioned medium may be separated by size exclusion. Any size exclusion matrix such as Sepharose may be used. As an example, a TSK Guard column SWXL, 6.times.40 mm or a TSK gel G4000 SWXL, 7.8.times.300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector. Fractions which are found to exhibit dynamic light scattering may be retained. For example, a fraction which is produced by the general method as described above, and which elutes with a retention time of 11-13 minutes, such as 12 minutes, is found to exhibit dynamic light scattering. The r.sub.h of particles in this peak is about 45-55 nm. Such fractions comprise mesenchymal stem cell particles such as exosomes.

Culture conditioned media may be concentrated by filtering/desalting means known in the art. In one embodiment Amicon filters, or substantially equivalent means, with specific molecular weight cut-offs are utilized, said cut-offs may select for molecular weights higher than 1 kDa to 50 kDa.

The cell culture supernatant may alternatively be concentrated using means known in the art such as solid phase extraction using C18 cartridges (Mini-Spe-ed C18-14%, S.P.E. Limited, Concord ON). Said cartridges are prepared by washing with methanol followed by deionized-distilled water. Up to 100 ml of stem cell or progenitor cell supernatant may be passed through each of these specific cartridges before elution, it is understood of one of skill in the art that larger cartridges may be used. After washing the cartridges material adsorbed is eluted with 3 ml methanol, evaporated under a stream of nitrogen, redissolved in a small volume of methanol, and stored at 4.degree. C.

Before testing the eluate for activity in vitro, the methanol is evaporated under nitrogen and replaced by culture medium. Said C18 cartridges are used to adsorb small hydrophobic molecules from the stem or progenitor cell culture supernatant, and allows for the elimination of salts and other polar contaminants. It may, however be desired to use other adsorption means in order to purify certain compounds from said fibroblast cell supernatant. Said fibroblast concentrated supernatant may be assessed directly for biological activities useful for the practice of this invention, or may be further purified. In one embodiment, said supernatant of fibroblast culture is assessed for ability to stimulate proteoglycan synthesis using an in vitro bioassay. Said in vitro bioassay allows for quantification and knowledge of which molecular weight fraction of supernatant possesses biological activity. Bioassays for testing ability to stimulate proteoglycan synthesis are known in the art. Production of various proteoglycans can be assessed by analysis of protein content using techniques including mass spectrometry, column chromatography, immune based assays such as enzyme linked immunosorbent assay (ELISA), immunohistochemistry, and flow cytometry.

Further purification may be performed using, for example, gel filtration using a Bio-Gel P-2 column with a nominal exclusion limit of 1800 Da (Bio-Rad, Richmond Calif.). Said column may be washed and pre-swelled in 20 mM Tris-HCl buffer, pH 7.2 (Sigma) and degassed by gentle swirling under vacuum. Bio-Gel P-2 material be packed into a 1.5.times.54 cm glass column and equilibrated with 3 column volumes of the same buffer. Amniotic fluid stem cell supernatant concentrates extracted by C18 cartridge may be dissolved in 0.5 ml of 20 mM Tris buffer, pH 7.2 and run through the column. Fractions may be collected from the column and analyzed for biological activity. Other purification, fractionation, and identification means are known to one skilled in the art and include anionic exchange chromatography, gas chromatography, high performance liquid chromatography, nuclear magnetic resonance, and mass spectrometry. Administration of supernatant active fractions may be performed locally or systemically.

In one embodiment lung progenitors are administered, together with mesenchymal stem cell exosomes and/or mesenchymal stem cell conditioned media. In one embodiment lung progenitor cells are characterized as having high expression of CD47 (CD47.sup.hi) from the pluripotent stem cell population, thereby isolating one or more lung progenitor cells. In one embodiment, the method further comprises sorting the population for low CD26 expression (CD26.sup.lo), such that an isolated population of CD47.sup.hi/CD26.sup.lo lung progenitor cells is isolated. In another embodiment of this aspect and all other aspects described herein, the at least one differentiation-inducing agent comprises at least one of CHIR 99021, BMP4, KGF, FGF10, and retinoic acid. In one embodiment, the concentration of CHIR 99021 used with the methods of generating primordial lung progenitors as described herein comprises at least 0.5 .mu.M, at least 1 .mu.M, at least 1.5 .mu.M, at least 2 .mu.M, at least 2.5 .mu.M, at least 3 .mu.M, at least 3.5 .mu.M, at least 4 .mu.M, at least 4.5 .mu.M, at least 5 .mu.M, at least 1004, at least 20 .mu.M or more. In another embodiment, the concentration of CHIR 99021 used with the methods of generating primordial lung progenitors as described herein comprises a concentration in the range of 1-5 .mu.M, 1-10 .mu.M, 1-20 .mu.M, 2-4 .mu.M, 5-20 .mu.M, 10-20 .mu.M, or any range there between. In another embodiment, the concentration of BMP4 used with the methods of generating primordial lung progenitors as described herein comprises at least 1 ng/mL, at least 2 ng/mL, at least 3 ng/mL, at least 4 ng/mL, at least 5 ng/mL, at least 6 ng/mL, at least 7 ng/mL, at least 8 ng/mL, at least 9 ng/mL, at least 10 ng/mL, at least 11 ng/mL, at least 12 ng/mL, at least 13 ng/mL, at least 14 ng/mL, at least 15 ng/mL, at least 20 ng/mL, at least 30 ng/mL, at least 40 ng/mL, at least 50 ng/mL, at least 60 ng/mL, at least 75 ng/mL, at least 100 ng/mL, at least 125 ng/mL, at least 150 ng/mL, at least 200 ng/mL or more. In another embodiment, the concentration of BMP4 used with the methods of generating primordial lung progenitors as described herein comprises a concentration in the range of 1-50 ng/mL, 1-25 ng/mL, 1-10 ng/mL, 5-10 ng/mL, 5-15 ng/mL, 5-25 ng/mL, 25-50 ng/mL, 25-75 ng/mL, 25-100 ng/mL, 25-150 ng/mL, 75-125 ng/mL or any range therebetween.

Another embodiment of the invention teaches isolating a lung progenitor cell for use with mesenchymal stem cell exosomes, the method comprising: (a) contacting a population of pluripotent cells with a first binding reagent that recognizes CD47 and a second binding reagent that recognizes CD26 to determine the level of expression of CD47 and CD26, and (b) isolating at least one cell with a cell surface phenotype comprising CD47.sup.hi/CD26.sup.lo, thereby isolating a lung progenitor cell from the population of pluripotent cells.

In another embodiment of this aspect and all other aspects described herein, the population of pluripotent cells is comprised by a tissue. Another embodiment teaches, the population of pluripotent cells is derived from induced pluripotent stem cells (IPSCs) in vitro. In another embodiment of this aspect and all other aspects described herein, the method further comprises a step of comparing the level of expression of CD47 and/or CD26 with a reference. In another embodiment of this aspect and all other aspects described herein, the lung progenitor cell also expresses NKX2-1.

EXAMPLES

Treg-JADI CELL™ Synergy in LPS Model

BALB/c mice, 5-7 weeks of age, females, were intraperitoneally injected with 50 mg/kg pentobarbital. Lipopolysaccharides (LPS) (5 mg/kg) (Sigma-Aldrich) was delivered to the lungs through a tracheostomy. Group 1 received LPS alone, Group 2, Umbilical blood Treg cells at 500,000 per mouse, Group 3 received JADI CELL™ 500,000 per mouse and Group 4 received the combination. Lung weight was compared to whole body weight. JADI CELL™ is a trade name for a population of plastic adherent, umbilical cord derived, mesenchymal stem cells positive for the following cellular markers: CD7, CD11, CD90, CD105, CD133, interleukin 1 receptor, interleukin 3 receptor, interleukin 6 receptor, interleukin 13 receptor, interleukin 17 receptor, interleukin 17F receptor, interleukin 10 receptor. Results are shown in FIG. 1.

Treg-JADI CELL™ Synergy in Poly IC Model

Figure 2:
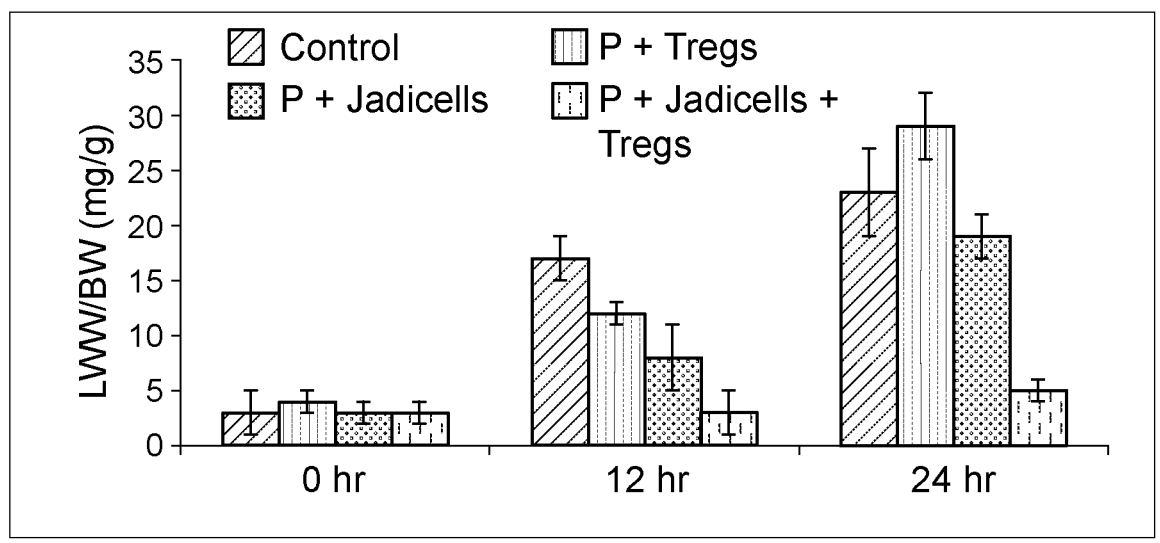
FIG. 2 is a bar graph showing Treg and JADI CELL™ Synergy in a Poly IC Model of BALB/c mice.

BALB/c mice, 5-7 weeks of age, females, were intraperitoneally injected with 50 mg/kg pentobarbital. Poly IC (1 mg/kg) (Sigma-Aldrich) was delivered to the lungs through a tracheostomy. Group 1 received Poly IC alone, Group 2, Umbilical blood Treg cells at 500,000 per mouse, Group 3 received JADI CELL™ 500,000 per mouse and Group 4 received the combination. Lung weight was compared to whole body weight. Results are shown in FIG. 2.

Treg-JADI CELL™ Synergy in LPS Model is Dependent on GITR

Figure 3:
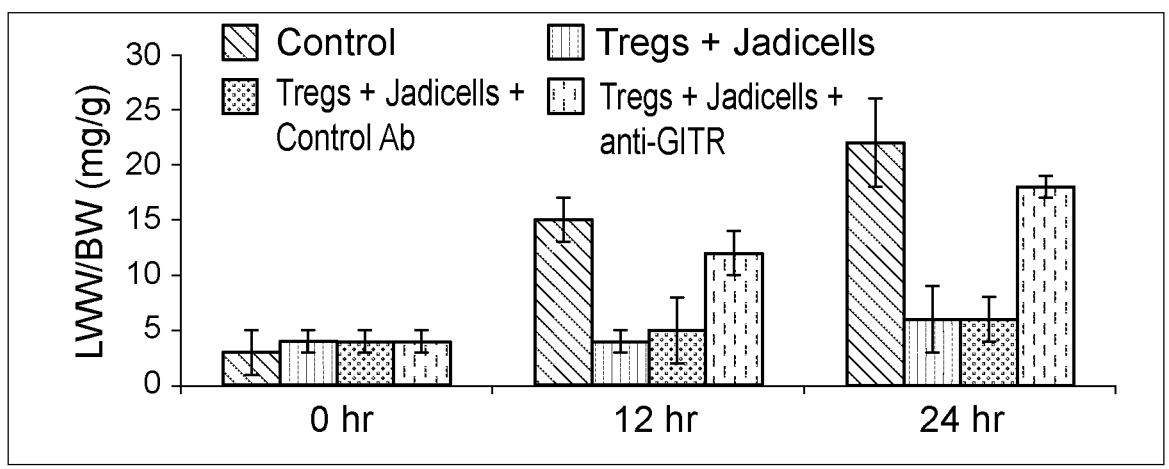
FIG. 3 is a bar graph showing Treg and JADI CELL™ Synergy in a LPS Model of BALB/c mice.

BALB/c mice, 5-7 weeks of age, females, were intraperitoneally injected with 50 mg/kg pentobarbital. Lipopolysaccharides (LPS) (5 mg/kg) (Sigma-Aldrich) was delivered to the lungs through a tracheostomy. Group 1 received LPS alone, Group 2, Umbilical blood Treg cells and JADI CELL™ at 500,000 per mouse, Group 3 received both cells and control antibody and Group 4 received both cells and anti-GITR. Lung weight was compared to whole body weight. Results are shown in FIG. 3.

REFERENCES

ADDIN EN.REFLIST 1. Zhu, N., et al., *A Novel Coronavirus from Patients with Pneumonia in China*, 2019. N Engl J Med, 2020. 382(8): p. 727-733.
2. Guo, Y. R., et al., *The origin, transmission and clinical therapies on coronavirus disease 2019 (COVID-19) outbreak-an update on the status*. Mil Med Res, 2020. 7(1): p. 11.

3. WHO, W.H.O., Coronavirus disease (COVID-19) outbreak 2020: p. www.who.int/emergencies/diseases/novel-coronavirus-2019.
4. Zhang, S., et al., *Estimation of the reproductive number of Novel Coronavirus (COVID-19) and the probable outbreak size on the Diamond Princess cruise ship: A data-driven analysis.* Int J Infect Dis, 2020.
5. Zhao, S., et al., *Preliminary estimation of the basic reproduction number of novel coronavirus (2019-nCoV) in China, from 2019 to 2020: A data-driven analysis in the early phase of the outbreak.* Int J Infect Dis, 2020. 92: p. 214-217.
6. Huang, C., et al., *Clinical features of patients infected with 2019 novel coronavirus in Wuhan, China.* Lancet, 2020. 395(10223): p. 497-506.
7. Wang, D., et al., *Clinical Characteristics of 138 Hospitalized Patients With 2019 Novel Coronavirus-Infected Pneumonia in Wuhan, China.* JAMA, 2020.
8. Chen, N., et al., *Epidemiological and clinical characteristics of 99 cases of 2019 novel coronavirus pneumonia in Wuhan, China: a descriptive study.* Lancet, 2020. 395(10223): p. 507-513.
9. Grasselli, G., A. Pesenti, and M. Cecconi, *Critical Care Utilization for the COVID-19 Outbreak in Lombardy, Italy: Early Experience and Forecast During an Emergency Response.* JAMA, 2020.
10. Wu, C., et al., *Risk Factors Associated With Acute Respiratory Distress Syndrome and Death in Patients With Coronavirus Disease 2019 Pneumonia in Wuhan, China.* JAMA Intern Med, 2020.
11. Shi, H., et al., *Radiological findings from 81 patients with COVID-19 pneumonia in Wuhan, China: a descriptive study.* Lancet Infect Dis, 2020.
12. Xu, Z., et al., *Pathological findings of COVID-19 associated with acute respiratory distress syndrome.* Lancet Respir Med, 2020.
13. Tian, S., et al., *Pulmonary pathology of early phase 2019 novel coronavirus (COVID-19) pneumonia in two patients with lung cancer.* J Thorac Oncol, 2020.
14. Zhao, T. X., et al., *Low-dose interleukin-2 in patients with stable ischaemic heart disease and acute coronary syndromes (LILACS): protocol and study rationale for a randomised, double-blind, placebo-controlled, phase I/II clinical trial.* BMJ Open, 2018. 8(9): p. e022452.
15. Jyonouchi, S., et al., *Phase I trial of low-dose interleukin 2 therapy in patients with Wiskott-Aldrich syndrome.* Clin Immunol, 2017. 179: p. 47-53.
16. Asano, T., et al., *Phase I/IIa Study of Low Dose Subcutaneous Interleukin-2 (IL-2) for Treatment of Refractory Chronic Graft Versus Host Disease.* Acta Med Okayama, 2016. 70(5): p. 429-433.
17. Kennedy-Nasser, A. A., et al., *Ultra low-dose IL-2 for GVHD prophylaxis after allogeneic hematopoietic stem cell transplantation mediates expansion of regulatory T cells without diminishing antiviral and antileukemic activity.* Clin Cancer Res, 2014. 20(8): p. 2215-25.
18. Mizui, M. and G. C. Tsokos, *Low-Dose IL-2 in the Treatment of Lupus.* Curr Rheumatol Rep, 2016. 18(11): p. 68.
19. Todd, J. A., et al., *Regulatory T Cell Responses in Participants with Type 1 Diabetes after a Single Dose of Interleukin-2: A Non-Randomised, Open Label, Adaptive Dose-Finding Trial.* PLoS Med, 2016. 13(10): p. e1002139.
20. Pham, M. N., M. G. von Herrath, and J. L. Vela, *Antigen-Specific Regulatory T Cells and Low Dose of IL-2 in Treatment of Type 1 Diabetes.* Front Immunol, 2015. 6: p. 651.
21. Waldron-Lynch, F., et al., *Rationale and study design of the Adaptive study of IL-2 dose on regulatory T cells in type 1 diabetes (DILT1D): a non-randomised, open label, adaptive dose finding trial.* BMJ Open, 2014. 4(6): p. e005559.
22. von Bahr, V., et al., *Mesenchymal stem cells may ameliorate inflammation in an ex vivo model of extracorporeal membrane oxygenation.* Perfusion, 2019. 34(1_suppl): p. 15-21.
23. Huppert, L. A., K. D. Liu, and M. A. Matthay, *Therapeutic potential of mesenchymal stromal cells in the treatment of ARDS.* Transfusion, 2019. 59(S1): p. 869-875.
24. Jung, Y. J., et al., *The effect of human adipose-derived stem cells on lipopolysaccharide-induced acute respiratory distress syndrome in mice.* Ann Transl Med, 2019. 7(22): p.
25. Chen, C. H., et al., *Effective protection against acute respiratory distress syndrome/sepsis injury by combined adipose-derived mesenchymal stem cells and preactivated disaggregated platelets.* Oncotarget, 2017. 8(47): p. 82415-82429.
26. Lu, H., et al., *Pulmonary Retention of Adipose Stromal Cells Following Intravenous Delivery Is Markedly Altered in the Presence of ARDS.* Cell Transplant, 2016. 25(9): p. 1635-1643.
27. Zheng, G., et al., *Treatment of acute respiratory distress syndrome with allogeneic adipose-derived mesenchymal stem cells: a randomized, placebo-controlled pilot study.* Respir Res, 2014. 15: p. 39.
28. Lu, Z., et al., *Mesenchymal stem cells induce dendritic cell immune tolerance via paracrine hepatocyte growth factor to alleviate acute lung injury.* Stem Cell Res Ther, 2019. 10(1): p. 372.
29. Silva, J. D., et al., *Mesenchymal Stromal Cells Are More Effective Than Their Extracellular Vesicles at Reducing Lung Injury Regardless of Acute Respiratory Distress Syndrome Etiology.* Stem Cells Int, 2019. 2019: p. 8262849.
30. Xu, A. L., et al., *Mesenchymal Stem Cells Reconditioned in Their Own Serum Exhibit Augmented Therapeutic Properties in the Setting of Acute Respiratory Distress Syndrome.* Stem Cells Transl Med, 2019. 8(10): p. 1092-1106.
31. Cardenes, N., et al., *Cell therapy for ARDS: efficacy of endobronchial versus intravenous administration and biodistribution of MAPCs in a large animal model.* BMJ Open Respir Res, 2019. 6(1): p. e000308.
32. Li, L., et al., *Mesenchymal stem cells with downregulated Hippo signaling attenuate lung injury in mice with lipopolysaccharide induced acute respiratory distress syndrome.* Int J Mol Med, 2019. 43(3): p. 1241-1252.
33. Mokhber Dezfouli, M. R., et al., *Intrapulmonary autologous transplant of bone marrow-derived mesenchymal stromal cells improves lipopolysaccharide-induced acute respiratory distress syndrome in rabbit.* Crit Care, 2018. 22(1): p. 353.
34. Schwede, M., et al., *Effects of bone marrow-derived mesenchymal stromal cells on gene expression in human alveolar type II cells exposed to TNF-alpha, IL-1 beta, and IFN-gamma.* Physiol Rep, 2018. 6(16): p. e13831.
35. Masterson, C., et al., *Syndecan-2-positive, Bone Marrow-derived Human Mesenchymal Stromal Cells Attenu-* ate *Bacterial-induced Acute Lung Injury and Enhance Resolution of Ventilator-induced Lung Injury in Rats.* Anesthesiology, 2018. 129(3): p. 502-516.
36. Park, J., et al., *Expression profile of microRNAs following bone marrow-derived mesenchymal stem cell treatment in lipopolysaccharide-induced acute lung injury.* Exp Ther Med, 2018. 15(6): p. 5495-5502.
37. Pedrazza, L., et al., *Mesenchymal stem cells improves survival in LPS-induced acute lung injury acting through inhibition of NETs formation.* J Cell Physiol, 2017. 232 (12): p. 3552-3564.
38. Yang, Y., et al., *The Vascular Endothelial Growth Factors-Expressing Character of Mesenchymal Stem Cells Plays a Positive Role in Treatment of Acute Lung Injury In Vivo.* Mediators Inflamm, 2016. 2016: p. 2347938.
39. Moodley, Y., et al., *Human mesenchymal stem cells attenuate early damage in a ventilated pig model of acute lung injury.* Stem Cell Res, 2016. 17(1): p. 25-31.
40. Hayes, M., et al., *Mesenchymal stromal cells are more effective than the MSC secretome in diminishing injury and enhancing recovery following ventilator-induced lung injury.* Intensive Care Med Exp, 2015. 3(1): p. 29.
41. Monsel, A., et al., *Therapeutic Effects of Human Mesenchymal Stem Cell-derived Microvesicles in Severe Pneumonia in Mice.* Am J Respir Crit Care Med, 2015. 192(3): p. 324-36.
42. Hao, Q., et al., *Study of Bone Marrow and Embryonic Stem Cell-Derived Human Mesenchymal Stem Cells for Treatment of Escherichia coli Endotoxin-Induced Acute Lung Injury in Mice.* Stem Cells Transl Med, 2015. 4(7): p. 832-40.
43. Devaney, J., et al., *Human mesenchymal stromal cells decrease the severity of acute lung injury induced by E. coli in the rat.* Thorax, 2015. 70(7): p. 625-35.
44. Asmussen, S., et al., *Human mesenchymal stem cells reduce the severity of acute lung injury in a sheep model of bacterial pneumonia.* Thorax, 2014. 69(9): p. 819-25.
45. Shalaby, S. M., et al., *Mesenchymal stromal cell injection protects against oxidative stress in Escherichia coli-induced acute lung injury in mice.* Cytotherapy, 2014. 16(6): p. 764-75.
46. Bustos, M. L., et al., *Activation of human mesenchymal stem cells impacts their therapeutic abilities in lung injury by increasing interleukin (IL)-10 and IL-1RN levels.* Stem Cells Transl Med, 2013. 2(11): p. 884-95.
47. Rojas, M., et al., *Infusion of freshly isolated autologous bone marrow derived mononuclear cells prevents endotoxin-induced lung injury in an ex-vivo perfused swine model.* Stem Cell Res Ther, 2013. 4(2): p. 26.
48. Yan, X., et al., *Nrf2/Keap1/ARE Signaling Mediated an Antioxidative Protection of Human Placental Mesenchymal Stem Cells of Fetal Origin in Alveolar Epithelial Cells.* Oxid Med Cell Longev, 2019. 2019: p. 2654910.
49. Cui, P., et al., *Human amnion-derived mesenchymal stem cells alleviate lung injury induced by white smoke inhalation in rats.* Stem Cell Res Ther, 2018. 9(1): p. 101.
50. Zhang, S., et al., *Nrf2 transfection enhances the efficacy of human amniotic mesenchymal stem cells to repair lung injury induced by lipopolysaccharide.* J Cell Biochem, 2018. 119(2): p. 1627-1636.
51. Huang, Z., et al., *Transcriptomic analysis of lung tissues after hUC-MSCs and FTY720 treatment of lipopolysaccharide-induced acute lung injury in mouse models.* Int Immunopharmacol, 2018. 63: p. 26-34.
52. Xuan, Y. Y., et al., *Human Mesenchymal Stem/Stromal Cells From Human Umbilical Cord Ameliorate Acute Respiratory Distress Syndrome in Rats: Factors to Consider.* Crit Care Med, 2017. 45(7): p. e736-e737.
53. Lee, F. Y., et al., *Xenogeneic human umbilical cord-derived mesenchymal stem cells reduce mortality in rats with acute respiratory distress syndrome complicated by sepsis.* Oncotarget, 2017. 8(28): p. 45626-45642.
54. Zhu, H., et al., *Therapeutic Effects of Human Umbilical Cord-Derived Mesenchymal Stem Cells in Acute Lung Injury Mice.* Sci Rep, 2017. 7: p. 39889.
55. Curley, G. F., et al., *Cryopreserved, Xeno-Free Human Umbilical Cord Mesenchymal Stromal Cells Reduce Lung Injury Severity and Bacterial Burden in Rodent Escherichia coli-Induced Acute Respiratory Distress Syndrome.* Crit Care Med, 2017. 45(2): p. e202-e212.
56. Chang, Y., et al., *Intratracheal administration of umbilical cord blood-derived mesenchymal stem cells in a patient with acute respiratory distress syndrome.* J Korean Med Sci, 2014. 29(3): p. 438-40.
57. Moodley, Y., et al., *Human umbilical cord mesenchymal stem cells reduce fibrosis of bleomycin-induced lung injury.* Am J Pathol, 2009. 175(1): p. 303-13.
58. Xiang, B., et al., *Transplantation of Menstrual Blood-Derived Mesenchymal Stem Cells Promotes the Repair of LPS-Induced Acute Lung Injury.* Int J Mol Sci, 2017. 18(4).
59. Wang, L., et al., *Lung-Resident Mesenchymal Stem Cells Promote Repair of LPS-Induced Acute Lung Injury via Regulating the Balance of Regulatory T cells and Th17 cells.* Inflammation, 2019. 42(1): p. 199-210.
60. Silva, J. D., et al., *Mesenchymal Stem Cells From Bone Marrow, Adipose Tissue, and Lung Tissue Differentially Mitigate Lung and Distal Organ Damage in Experimental Acute Respiratory Distress Syndrome.* Crit Care Med, 2018. 46(2): p. e132-e140.
61. Su, V. Y., et al., *Mesenchymal Stem Cell-Conditioned Medium Induces Neutrophil Apoptosis Associated with Inhibition of the NF-kappaB Pathway in Endotoxin-Induced Acute Lung Injury.* Int J Mol Sci, 2019. 20(9).
62. Mohammadipoor, A., et al., *Therapeutic potential of products derived from mesenchymal stem/stromal cells in pulmonary disease.* Respir Res, 2018. 19(1): p. 218.
63. Lee, J. H., J. Park, and J. W. Lee, *Therapeutic use of mesenchymal stem cell-derived extracellular vesicles in acute lung injury.* Transfusion, 2019. 59(S1): p. 876-883.
64. Abreu, S. C., D. J. Weiss, and P. R. Rocco, *Extracellular vesicles derived from mesenchymal stromal cells: a therapeutic option in respiratory diseases?* Stem Cell Res Ther, 2016. 7(1): p. 53.
65. Monsel, A., et al., *Mesenchymal stem cell derived secretome and extracellular vesicles for acute lung injury and other inflammatory lung diseases.* Expert Opin Biol Ther, 2016. 16(7): p. 859-71.
66. Liu, F. B., Q. Lin, and Z. W. Liu, *A study on the role of apoptotic human umbilical cord mesenchymal stem cells in bleomycin-induced acute lung injury in rat models.* Eur Rev Med Pharmacol Sci, 2016. 20(5): p. 969-82.
67. Chen, J., et al., *Mesenchymal Stem Cell Conditioned Medium Promotes Proliferation and Migration of Alveolar Epithelial Cells under Septic Conditions In Vitro via the JNK-P38 Signaling Pathway.* Cell Physiol Biochem, 2015. 37(5): p. 1830-46.
68. Ionescu, L., et al., *Stem cell conditioned medium improves acute lung injury in mice: in vivo evidence for stem cell paracrine action.* Am J Physiol Lung Cell Mol Physiol, 2012. 303(11): p. L967-77.

69. Court, A. C., et al., *Mitochondrial transfer from MSCs to T cells induces Treg differentiation and restricts inflammatory response.* EMBO Rep, 2020. 21(2): p. e48052.
70. Liu, Y., et al., *Human umbilical cord mesenchymal stem cells confer potent immunosuppressive effects in Sjogren's syndrome by inducing regulatory T cells.* Mod Rheumatol, 2020: p. 1-11.
71. Fakhimi, M., et al., *Helios, CD73 and CD39 Induction in Regulatory T Cells Exposed to Adipose Derived Mesenchymal Stem Cells.* Cell J, 2020. 22(2): p. 236-244.
72. Khosravi, M., et al., *Induction of CD4(+)CD25(+)FOXP3(+) regulatory T cells by mesenchymal stem cells is associated with modulation of ubiquitination factors and TSDR demethylation.* Stem Cell Res Ther, 2018. 9(1): p. 273.
73. Roux, C., et al., *Immunosuppressive Mesenchymal Stromal Cells Derived from Human-Induced Pluripotent Stem Cells Induce Human Regulatory T Cells In Vitro and In Vivo.* Front Immunol, 2017. 8: p. 1991.
74. Miyagawa, I., et al., *Regulatory Mechanism of The Induction of Regulatory T Cells through Growth Factors Released by Human Mesenchymal Stem Cells.* Crit Rev Immunol, 2018. 38(6): p. 471-478.
75. Khosravi, M., et al., *Induction of CD4(+)CD25(+)Foxp3(+) regulatory T cells by mesenchymal stem cells is associated with RUNX complex factors.* Immunol Res, 2018. 66(1): p. 207-218.
76. Khosravi, M., et al., *Mesenchymal stem cells can induce regulatory T cells via modulating miR-126a but not miR-10a.* Gene, 2017. 627: p. 327-336.
77. Lee, H. J., et al., *ICOSL expression in human bone marrow-derived mesenchymal stem cells promotes induction of regulatory T cells.* Sci Rep, 2017. 7: p. 44486.
78. Chen, C., et al., *Mesenchymal stem cells upregulate Treg cells via sHLA-G in SLE patients.* Int Immunopharmacol, 2017. 44: p. 234-241.
79. Lim, J. Y., et al., *Enhanced immunoregulation of mesenchymal stem cells by IL producing type 1 regulatory T cells in collagen-induced arthritis.* Sci Rep, 2016. 6: p. 26851.
80. Lee, E. S., et al., *Adoptive Transfer of Treg Cells Combined with Mesenchymal Stem Cells Facilitates Repopulation of Endogenous Treg Cells in a Murine Acute GVHD Model.* PLoS One, 2015. 10(9): p. e0138846.
81. Cahill, E. F., et al., *Jagged-1 is required for the expansion of CD4+ CD25+ FoxP3+ regulatory T cells and tolerogenic dendritic cells by murine mesenchymal stromal cells.* Stem Cell Res Ther, 2015. 6: p. 19.
82. Wang, Z. X., et al., *Mesenchymal stem cells alleviate atherosclerosis by elevating number and function of CD4(+)CD25 (+)FOXP3 (+) regulatory T-cells and inhibiting macrophage foam cell formation.* Mol Cell Biochem, 2015. 400(1-2): p. 163-72.
83. Takahashi, T., et al., *Multipotent mesenchymal stromal cells synergize with costimulation blockade in the inhibition of immune responses and the induction of Foxp3+ regulatory T cells.* Stem Cells Transl Med, 2014. 3(12): p. 1484-94.
84. Frazier, T. P., et al., *Human adipose-derived stromal/stem cells induce functional CD4+CD25+FoxP3+CD127− regulatory T cells under low oxygen culture conditions.* Stem Cells Dev, 2014. 23(9): p. 968-77.
85. Li, J. G., et al., *Human mesenchymal stem cells elevate CD4+CD25+CD127low/− regulatory T cells of asthmatic patients via heme oxygenase-1.* Iran J Allergy Asthma Immunol, 2013. 12(3): p. 228-35.
86. Luz-Crawford, P., et al., *Mesenchymal stem cells generate a CD4+CD25+Foxp3+ regulatory T cell population during the differentiation process of Th1 and Th17 cells.* Stem Cell Res Ther, 2013. 4(3): p. 65.
87. Melief, S. M., et al., *Multipotent stromal cells induce human regulatory T cells through a novel pathway involving skewing of monocytes toward anti-inflammatory macrophages.* Stem Cells, 2013. 31(9): p. 1980-91.
88. Erkers, T., et al., *Decidual stromal cells promote regulatory T cells and suppress alloreactivity in a cell contact-dependent manner.* Stem Cells Dev, 2013. 22(19): p. 2596-605.
89. Engela, A. U., et al., *Human adipose-tissue derived mesenchymal stem cells induce functional de-novo regulatory T cells with methylated FOXP3 gene DNA.* Clin Exp Immunol, 2013. 173(2): p. 343-54.
90. Tasso, R., et al., *Mesenchymal stem cells induce functionally active T-regulatory lymphocytes in a paracrine fashion and ameliorate experimental autoimmune uveitis.* Invest Ophthalmol Vis Sci, 2012. 53(2): p. 786-93.
91. Choi, Y. S., J. A. Jeong, and D. S. Lim, *Mesenchymal stem cell-mediated immature dendritic cells induce regulatory T cell-based immunosuppressive effect.* Immunol Invest, 2012. 41(2): p. 214-29.
92. Sun, J., et al., *Intrapulmonary delivery of human umbilical cord mesenchymal stem cells attenuates acute lung injury by expanding CD4+CD25+ Forkhead Boxp3 (FOXP3)+ regulatory T cells and balancing anti-and pro-inflammatory factors.* Cell Physiol Biochem, 2011. 27(5): p. 587-96.
93. Madec, A. M., et al., *Mesenchymal stem cells protect NOD mice from diabetes by inducing regulatory T cells.* Diabetologia, 2009. 52(7): p. 1391-9.
94. English, K., et al., *Cell contact, prostaglandin E(2) and transforming growth factor beta 1 play non-redundant roles in human mesenchymal stem cell induction of CD4+CD25(High) forkhead box P3+ regulatory T cells.* Clin Exp Immunol, 2009. 156(1): p. 149-60.
95. Gonzalez-Rey, E., et al., *Human adipose-derived mesenchymal stem cells reduce inflammatory and T cell responses and induce regulatory T cells in vitro in rheumatoid arthritis.* Ann Rheum Dis, 2010. 69(1): p. 241-8.
96. Casiraghi, F., et al., *Pretransplant infusion of mesenchymal stem cells prolongs the survival of a semiallogeneic heart transplant through the generation of regulatory T cells.* J Immunol, 2008. 181(6): p. 3933-46.
97. Prevosto, C., et al., *Generation of CD4+ or CD8+ regulatory T cells upon mesenchymal stem cell-lymphocyte interaction.* Haematologica, 2007. 92(7): p. 881-8.
98. Hirsch, R., J. D. Ellenhorn, and J. A. Bluestone, *In vivo administration of anti-CD3 monoclonal antibody can activate immune responses thus preventing malignant tumor growth.* Princess Takamatsu Symp, 1988. 19: p. 237-43.
99. Schoof, D. D., et al., *Activation of human tumor-infiltrating lymphocytes by monoclonal antibodies directed to the CD3 complex.* Cancer Res, 1990. 50(4): p. 1138-43.
100. Davis, L. S., M. C. Wacholtz, and P. E. Lipsky, *The induction of T cell unresponsiveness by rapidly modulating CD3.* J Immunol, 1989. 142(4): p. 1084-94.
101. Anasetti, C., et al., *Induction of specific nonresponsiveness in unprimed human T cells by anti-CD3 antibody and alloantigen.* J Exp Med, 1990. 172(6): p. 1691-700.
102. Woodle, E. S., et al., *Phase I trial of a humanized, Fc receptor nonbinding OKT3 antibody, huOKT3gamma1*

(Ala-Ala) in the treatment of acute renal allograft rejection. Transplantation, 1999. 68(5): p. 608-16.
103. Cosimi, A. B., et al., Treatment of acute renal allograft rejection with OKT3 monoclonal antibody. Transplantation, 1981. 32(6): p. 535-9.
104. Ortho Multicenter Transplant Study, G., A randomized clinical trial of OKT3 monoclonal antibody for acute rejection of cadaveric renal transplants. N Engl J Med, 1985. 313(6): p. 337-42.
105. Debure, A., et al., One-month prophylactic use of OKT3 in cadaver kidney transplant recipients. Transplantation, 1988. 45(3): p. 546-53.
106. Oh, H. K., et al., Two low-dose OKT3 induction regimens following renal transplantation—clinical experience at a single center. Clin Transplant, 1998. 12(4): p. 343-7.
107. Opelz, G., Efficacy of rejection prophylaxis with OKT3 in renal transplantation. Collaborative Transplant Study. Transplantation, 1995. 60(11): p. 1220-4.
108. Darby, C. R., et al., Reduced dose OKT3 prophylaxis in sensitised kidney recipients. Transpl Int, 1996. 9(6): p. 565-9.
109. Ciancio, G., et al., Human donor bone marrow cells can enhance hyporeactivity in renal transplantation using maintenance FK 506 and OKT3 induction therapy. Transplant Proc, 1996. 28(2): p. 943-4.
110. Waid, T. H., et al., Treatment of renal allograft rejection with T10B9.1A31 or OKT3: final analysis of a phase II clinical trial. Transplantation, 1997. 64(2): p. 274-81.
111. Kumar, M. S., et al., ATGAM versus OKT3 induction therapy in cadaveric kidney transplantation: patient and graft survival, CD3 subset, infection, and cost analysis. Transplant Proc, 1998. 30(4): p. 1351-2.
112. Cosimi, A. B., et al., A randomized clinical trial comparing OKT3 and steroids for treatment of hepatic allograft rejection. Transplantation, 1987. 43(1): p. 91-5.
113. Millis, J. M., et al., Randomized prospective trial of OKT3 for early prophylaxis of rejection after liver transplantation. Transplantation, 1989. 47(1): p. 82-8.
114. Whiting, J. F., et al., Use of low-dose OKT3 as induction therapy in liver transplantation. Transplantation, 1998. 65(4): p. 577-80.
115. Melzer, J. S., et al., The use of OKT3 in combined pancreas-kidney allotransplantation. Transplant Proc, 1990. 22(2): p. 634-5.
116. Sindhi, R., et al., Increased risk of pulmonary edema in diabetic patients undergoing preemptive pancreas transplantation with OKT3 induction. Transplant Proc, 1995. 27(6): p. 3016-7.
117. Stratta, R. J., et al., A prospective randomized trial of OKT3 vs ATGAM induction therapy in pancreas transplant recipients. Transplant Proc, 1996. 28(2): p. 917-8.
118. Ross, D. J., et al., Delayed development of obliterative bronchiolitis syndrome with OKT3 after unilateral lung transplantation. A plea for multicenter immunosuppressive trials. Chest, 1996. 109(4): p. 870-3.
119. van Gelder, T., et al., A randomized trial comparing safety and efficacy of OKT3 and a monoclonal anti-interleukin-2 receptor antibody (BT563) in the prevention of acute rejection after heart transplantation. Transplantation, 1996. 62(1): p. 51-5.
120. Delgado, J. F., et al., Induction treatment with monoclonal antibodies for heart transplantation. Transplant Rev (Orlando), 2011. 25(1): p. 21-6.
121. Kormos, R. L., et al., Monoclonal versus polyclonal antibody therapy for prophylaxis against rejection after heart transplantation. J Heart Transplant, 1990. 9(1): p. 1-9, discussion 9-10.
122. Rabinov, M., et al., Recipient selection algorithm for immunosuppression in cardiac transplantation: OKT3 vs triple therapy alone. Transplant Proc, 1992. 24(1): p. 167-8.
123. Chin, C., et al., Induction therapy for pediatric and adult heart transplantation: comparison between OKT3 and daclizumab. Transplantation, 2005. 80(4): p. 477-81.
124. Prentice, H. G., et al., Use of anti-T-cell monoclonal antibody OKT3 to prevent acute graft-versus-host disease in allogeneic bone-marrow transplantation for acute leukaemia. Lancet, 1982. 1(8274): p. 700-3.
125. Weinshenker, B. G., et al., An open trial of OKT3 in patients with multiple sclerosis. Neurology, 1991. 41(7): p. 1047-52.
126. Herold, K. C., et al., A single course of anti-CD3 monoclonal antibody hOKT3gamma1(Ala-Ala) results in improvement in C-peptide responses and clinical parameters for at least 2 years after onset of type 1 diabetes. Diabetes, 2005. 54(6): p. 1763-9.
127. Ferran, C., et al., Cytokine-related syndrome following injection of anti-CD3 monoclonal antibody: further evidence for transient in vivo T cell activation. Eur J Immunol, 1990. 20(3): p. 509-15.
128. Vasquez, E. M., A. J. Fabrega, and R. Pollak, OKT3-induced cytokine-release syndrome: occurrence beyond the second dose and association with rejection severity. Transplant Proc, 1995. 27(1): p. 873-4.
129. Norman, D. J., J. A. Kimball, and J. M. Barry, Cytokine-release syndrome: differences between high and low doses of OKT3. Transplant Proc, 1993. 25(2 Suppl 1): p. 35-8.
130. Goldman, M., et al., OKT3-induced cytokine release attenuation by high-dose methylprednisolone. Lancet, 1989. 2(8666): p. 802-3.
131. Fletcher, E. A. K., et al., Extracorporeal human whole blood in motion, as a tool to predict first-infusion reactions and mechanism-of-action of immunotherapeutics. Int Immunopharmacol, 2018. 54: p. 1-11.
132. Chatenoud, L., et al., In vivo cell activation following OKT3 administration. Systemic cytokine release and modulation by corticosteroids. Transplantation, 1990. 49(4): p. 697-702.
133. Chatenoud, L., et al., Corticosteroid inhibition of the OKT3-induced cytokine-related syndrome—dosage and kinetics prerequisites. Transplantation, 1991. 51(2): p. 334-8.
134. Bugelski, P. J., et al., Monoclonal antibody-induced cytokine-release syndrome. Expert Rev Clin Immunol, 2009. 5(5): p. 499-521.
135. Barel, D., et al., Enhanced tumor necrosis factor in anti-CD3 antibody stimulated diabetic NOD mice: modulation by PGE1 and dietary lipid. Autoimmunity, 1992. 13(2): p. 141-9.
136. Pradier, O., et al., Procoagulant effect of the OKT3 monoclonal antibody: involvement of tumor necrosis factor. Kidney Int, 1992. 42(5): p. 1124-9.
137. Wissing, K. M., et al., A pilot trial of recombinant human interleukin-10 in kidney transplant recipients receiving OKT3 induction therapy. Transplantation, 1997. 64(7): p. 999-1006.
138. Charpentier, B., et al., Evidence that antihuman tumor necrosis factor monoclonal antibody prevents OKT3-induced acute syndrome. Transplantation, 1992. 54(6): p. 997-1002.

139. DeVault, G. A., Jr., et al., *The effects of oral pentoxifylline on the cytokine release syndrome during inductive OKT3*. Transplantation, 1994. 57(4): p. 532-40.
140. Ilan, Y., et al., *Oral administration of OKT3 monoclonal antibody to human subjects induces a dose-dependent immunologic effect in T cells and dendritic cells*. J Clin Immunol, 2010. 30(1): p. 167-77.
141. Lalazar, G., et al., *Oral Administration of OKT3 MAb to Patients with NASH, Promotes Regulatory T-cell Induction, and Alleviates Insulin Resistance: Results of a Phase IIa Blinded Placebo-Controlled Trial*. J Clin Immunol, 2015. 35(4): p. 399-407.
142. Roten, R., et al., *Plasma levels of tumor necrosis factor in the adult respiratory distress syndrome*. Am Rev Respir Dis, 1991. 143(3): p. 590-2.
143. Sheng, W. H., et al., *Clinical manifestations and inflammatory cytokine responses in patients with severe acute respiratory syndrome*. J Formos Med Assoc, 2005. 104(10): p.
144. Romaschin, A. D., et al., *Systemic phospholipase A2 and cachectin levels in adult respiratory distress syndrome and multiple-organ failure*. Clin Biochem, 1992. 25(1): p. 55-60.
145. Koh, Y., et al., *Tumor necrosis factor induced acute lung leak in rats: less than with interleukin-1*. Inflammation, 1996. 20(5): p. 461-9.
146. Dunican, A. L., et al., *TNFalpha-induced suppression of PMN apoptosis is mediated through interleukin-8 production*. Shock, 2000. 14(3): p. 284-8; discussion 288-9.
147. Negrier, M. S., et al., *Phase I trial of recombinant interleukin-2 followed by recombinant tumor necrosis factor in patients with metastatic cancer*. J Immunother (1991), 1992. 11(2): p. 93-102.
148. Malemud, C. J., *Recent advances in neutralizing the IL-6 pathway in arthritis*. Open Access Rheumatol, 2009. 1: p. 133-150.
149. Romagnani, S., *Human Th17 cells*. Arthritis Res Ther, 2008. 10(2): p. 206.
150. Romagnani, S., et al., *Properties and origin of human Th17 cells*. Mol Immunol, 2009. 47(1): p. 3-7.
151. Kimura, A. and T. Kishimoto, *IL-6: regulator of Treg/Th17 balance*. Eur J Immunol, 2010. 40(7): p. 1830-5.
152. Yu, Z. X., et al., *The ratio of Th17/Treg cells as a risk indicator in early acute respiratory distress syndrome*. Crit Care, 2015. 19: p. 82.
153. Mock, J. R., et al., *Foxp3+ regulatory T cells promote lung epithelial proliferation*. Mucosal Immunol, 2014. 7(6): p. 1440-51.
154. Kimura, A. and T. Kishimoto, *Th17 cells in inflammation*. Int Immunopharmacol, 2011. 11(3): p. 319-22.
155. Meduri, G. U., et al., *Persistent elevation of inflammatory cytokines predicts a poor outcome in ARDS. Plasma IL-1 beta and IL-6 levels are consistent and efficient predictors of outcome over time*. Chest, 1995. 107(4): p. 1062-73.
156. Hui, L., et al., *Higher serum procalcitonin and IL-6 levels predict worse diagnosis for acute respiratory distress syndrome patients with multiple organ dysfunction*. Int J Clin Exp Pathol, 2017. 10(7): p. 7401-7407.
157. Swaroopa, D., et al., *Association of serum interleukin-6, interleukin-8, and Acute Physiology and Chronic Health Evaluation II score with clinical outcome in patients with acute respiratory distress syndrome*. Indian J Crit Care Med, 2016. 20(9): p. 518-25.
158. Bime, C., et al., *Development of a biomarker mortality risk model in acute respiratory distress syndrome*. Crit Care, 2019. 23(1): p. 410.
159. Spadaro, S., et al., *Biomarkers for Acute Respiratory Distress syndrome and prospects for personalised medicine*. J Inflamm (Lond), 2019. 16: p. 1.
160. Nakamoto, S., *Reflections on My Lifetime Teacher: Dr. Willem J. Kolff*. Artif Organs, 2018. 42(2): p. 115-126.
161. Krakauer, R. S., et al., *Circulating immune complexes in rheumatoid arthritis. Selective removal by cryogelation with membrane filtration*. Arch Intern Med, 1982. 142(2): p. 395-7.
162. Snyder, H. W., Jr., et al., *Clearance of feline leukemia virus from persistently infected pet cats treated by extracorporeal immunoadsorption is correlated with an enhanced antibody response to FeLV gp 70*. J Immunol, 1984. 132(3): p. 1538-43.
163. Hellstrom, K. E., et al., *Blocking (suppressor) factors, immune complexes, and extracorporeal immunoadsorption in tumor immunity*. Contemp Top Immunobiol, 1985.
164. Messerschmidt, G. L., et al., *Protein A immunoadsorption in the treatment of malignant disease*. J Clin Oncol, 1988. 6(2): p. 203-12.
165. Cameron, D. J., C. T. Fitts, and P. R. Rajagopalan, *Antigen-coated immunoadsorbents utilized for in vivo depletion of antibodies and lymphocytes with specificity for the antigen*. J Surg Oncol, 1983. 23(3): p. 158-62.
166. Lazaridis, K., et al., *Specific removal of autoantibodies by extracorporeal immunoadsorption ameliorates experimental autoimmune myasthenia gravis*. J Neuroimmunol, 2017. 312: p. 24-30.
167. Lupinek, C., et al., *Extracorporeal IgE Immunoadsorption in Allergic Asthma: Safety and Efficacy*. EBioMedicine, 2017. 17: p. 119-133.
168. Fabbrini, P., et al., *Light chains removal by extracorporeal techniques in acute kidney injury due to multiple myeloma: a position statement of the Onconephrology Work Group of the Italian Society of Nephrology*. J Nephrol, 2016. 29(6): p. 735-746.
169. Opgenoorth, M., et al., *Treatment of antibody-mediated rejection including immunoadsorption during first year after renal transplantation—Clinical results and regulation of endothelial progenitor cells*. Atheroscler Suppl, 2015. 18: p. 67-73.
170. Lazaridis, K., et al., *Antigen-specific apheresis of autoantibodies in myasthenia gravis*. Ann N Y Acad Sci, 2012. 1275: p. 7-12.
171. Koch, B., S. Buttner, and H. Geiger, [*Reducing viral load in life-threatening viral diseases using snowdrops*]. Dtsch Med Wochenschr, 2016. 141(25): p. 1868-1871.
172. Koch, B., et al., *Lectin Affinity Plasmapheresis for Middle East Respiratory Syndrome-Coronavirus and Marburg Virus Glycoprotein Elimination*. Blood Purif, 2018. 46(2): p. 126-133.
173. Moriyama, M., et al., *Removal of hepatitis C virus by G-1 beads in sera from patients with chronic hepatitis C*. Intervirology, 2005. 48(2-3): p. 84-8.
174. Josephs, S. F., et al., *Unleashing endogenous TNF-alpha as a cancer immunotherapeutic*. J Transl Med, 2018. 16(1): p. 242.
175. Kanekura, T., et al., *Granulocyte and monocyte adsorption apheresis (GCAP) for refractory skin diseases caused by activated neutrophils and psoriatic arthritis: evidence that GCAP removes Mac-1-expressing neutrophils*. Ther Apher Dial, 2006. 10(3): p. 247-56.

176. Nakane, S., et al., *Cytapheresis with a filter for selective removal of CD4+ T cells in experimental autoimmune encephalomyelitis*. Mult Scler, 2003. 9(6): p. 579-84.

The invention claimed is:

1. A method of inhibiting lung inflammation comprising:
   a) identying a subject suffering from lung inflammation;
   b) administering a population of T regulatory cells in combination with a population of plastic adherent umbilical cord derived mesenchymal stem cells in an amount sufficient to reduce inflammation in said subject's lungs.

2. The method of claim 1, wherein said T regulatory cells are derived from umbilical blood.

3. The method of claim 1, wherein said T regulatory cells express glucocorticoid-induced tumor necrosis factor receptor-related (GITR).

4. The method of claim 3, wherein said T regulatory cells express GITR at a higher percentage than average T regulatory cells.

5. The method of claim 1, wherein said mesenchymal stem cell population expresses the following cellular markers: CD7, CD11, CD90, CD105, CD133, interleukin 1 receptor, interleukin 3 receptor, interleukin 6 receptor, interleukin 13 receptor, interleukin 17 receptor, interleukin 17F receptor, interleukin 10 receptor.

6. The method of claim 1, wherein said mesenchymal stem cell population is pretreated with an activator of indolamine 2-3 deoxygenase.

7. The method of claim 6, wherein said activator of indolamine 2-3 deoxygenase is selected from a group comprising of: a) interferon alpha; b) interferon gamma; c) interferon beta; and d) interleukin 33.

8. The method of claim 1, wherein said lung inflammation is from acute respiratory distress syndrome (ARDS).

9. The method of claim 8, wherein said ARDS is caused by COVID-19.

10. The method of claim 1, wherein said lung inflammation is lung fibrosis.

11. The method of claim 2, wherein said T regulatory cells express Glucocorticoid-Induced tumor necrosis factor receptor-Related (GITR) TGF-beta.

12. The method of claim 11, wherein said T regulatory cells express GITR at a higher percentage than average T regulatory cells.

* * * * *